United States Patent [19]

Cellitti et al.

[11] 4,412,752
[45] Nov. 1, 1983

[54] METHOD AND APPARATUS FOR DETERMINING THE COOLING CHARACTERISTICS OF A QUENCHING MEDIUM

[75] Inventors: Raymond A. Cellitti, Hinsdale; John J. Connelly, Naperville, both of Ill.

[73] Assignee: International Harvester Co., Chicago, Ill.

[21] Appl. No.: 303,812

[22] Filed: Sep. 21, 1981

[51] Int. Cl.³ ............................................. G01N 25/00
[52] U.S. Cl. ........................................ 374/43; 374/54
[58] Field of Search ...................... 374/43, 44, 45, 53, 374/54; 364/472, 477

[56] References Cited

U.S. PATENT DOCUMENTS

| | | | |
|---|---|---|---|
| 2,587,622 | 3/1952 | Jaffe | 374/43 |
| 2,717,515 | 9/1955 | Pesante | 374/43 |
| 2,730,894 | 1/1956 | Husa | 374/43 |
| 3,013,427 | 12/1961 | Bender | 374/43 |
| 3,620,068 | 11/1971 | Cary et al. | 374/43 |
| 3,981,175 | 9/1976 | Hammond | 374/10 |

*Primary Examiner*—Herbert Goldstein
*Attorney, Agent, or Firm*—John P. O'Brien; F. David Aubuchon

[57] ABSTRACT

A method and apparatus for determining the cooling characteristics of a quenching medium includes a temperature probe having a predetermined thermal mass and conductivity and a temperature sensor affixed to the probe. The probe and sensor are heated to a predetermined temperature and immersed in the quenching medium. The output of the temperature sensor is applied to a microcomputer that has been programmed to monitor the quench rate and to determine whether the quench rate is within predetermined limits at predetermined temperatures.

1 Claim, 3 Drawing Figures

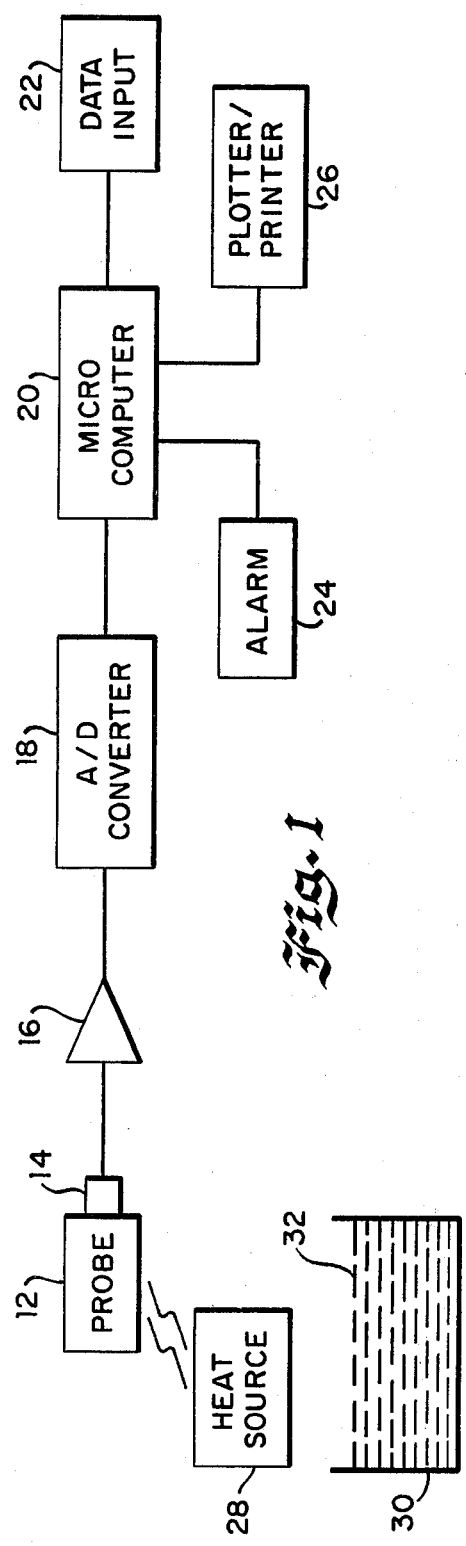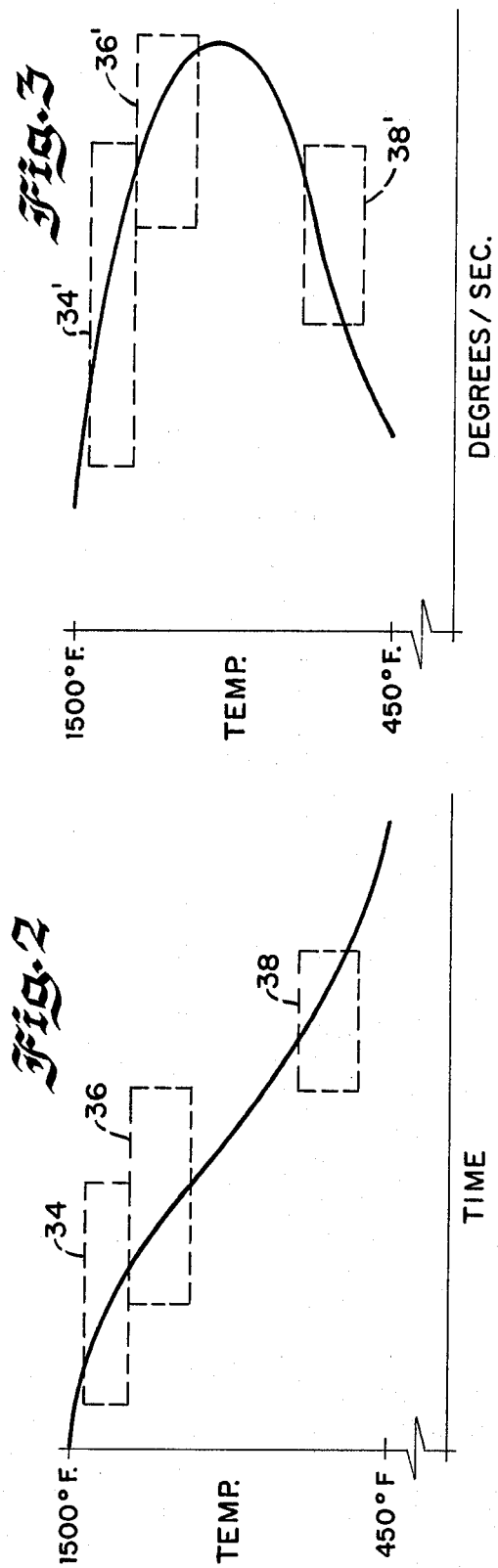

METHOD AND APPARATUS FOR DETERMINING THE COOLING CHARACTERISTICS OF A QUENCHING MEDIUM

BACKGROUND OF THE INVENTION

1. Field of the Invention

This invention relates generally to quenching of heat treated materials, and more particularly, to a method and apparatus for automatically determining whether the quenchant being employed is performing the quenching operation satisfactorily.

2. Description of the Prior Art

Quenching systems are known. Typical prior art quenching systems typically utilize a quenching medium such as water, oil, brine or the like, or mixtures thereof, to quench heated work pieces at predetermined quenching rates to obtain certain desired metallurgical characteristics.

While prior art quenching systems generally do produce parts or components having the desired metallurgical characteristics, the quantity of the parts being produced tends to deteriorate as the quenching medium becomes contaminated or otherwise changes or degrades. Also, when a newly designed part is first manufactured, in many instances, the determination of the proper quenchant to obtain the desired metallurgical characteristics is a matter of trial and error, and once the proper quenching medium has been established, its characteristics are still subject to the previously mentioned changes. Both of the above-mentioned factors can result in improper quenching, and the results of such improper quenching would not become apparent until the characteristics of the quenched work pieces were metallurgically examined. Consequently, many improperly quenched components could be manufactured before the improper quenching was detected.

Because the purpose of quenching is to obtain certain desired phases in the quenched medium, for example, austenite, bainite and pearlite in ferrous materials, the earliest prior art methods for determining whether the quenching medium was operating properly simply utilized a physical or metallurgical examination of the quenched parts being manufactured. Later systems monitored the cooling characteristics of the part being quenched and looked for a "dwell" in the cooling curve indicative of a change in phase of the material being quenched. Typical of such prior art patents are U.S. Pat. Nos. 3,981,834; 4,088,974; 4,133,036 and 4,187,541. However, such systems are more applicable to determining the cooling characteristics of the material being cooled to determine if desired transformtions had taken place, rather than to checking the performance of the quenching medium itself.

SUMMARY OF THE INVENTION

Accordingly, it is an object of the present invention to provide a quenching system that overcomes many of the disadvantages of the prior art quenching systems.

It is another object of the present invention to provide a method and apparatus for determining the cooling characteristics of a quenching medium.

It is still another object of the present invention to provide a system for automatically plotting the cooling characteristics of a quenching medium.

It is yet another object of the present invention to provide apparatus for automatically providing an alarm indication if the cooling characteristics of a quenching medium are not within predetermined specified boundaries.

It is still another object of the present invention to provide a design tool to aid in component design and in the prior selection of a quenching medium for such newly designed components.

Therefore, in accordance with a preferred embodiment of the invention, a known probe containing a temperature sensor is heated to a predetermined temperature and immersed in the quenching medium to be tested. The output of the temperature sensing probe is monitored by a computing system, such as a microcomputer or the like, and the cooling rate of the probe is computed at various temperatures. The cooling rate thus computed is compared with data representative of the desired cooling rates at various temperatures, and an alarm condition indicative of an inadequate quenching medium is generated if the cooling rate thus determined deviates from the desired cooling rate by more than a predetermined increment.

DESCRIPTION OF THE DRAWING

These and other objects and advantages of the present invention will be readily apparent upon consideration of the following detailed description and attached drawing, wherein:

FIG. 1 is a block diagram of the system according to the invention;

FIG. 2 is a graph of a typical temperature versus time cooling curve of a typical probe; and FIG. 3 is a graph showing the cooling rate of the same probe as a function of temperature.

DETAILED DESCRIPTION OF THE PREFERRED

The system according to the invention is generally designated in FIG. 1 by the reference numeral 10, and contains a probe 12, a temperature sensor 14, an analog-to-digital converter 18, a microcomputer 20, a data input terminal 22 for the microcomputer 20, and a display 26 which may be a plotter, printer or other suitable display, such as, for example, a cathode ray tube display. A heat source 28 which may be an oven or any suitable heat source (including an electrical resistance heater in the probe itself or the same oven used to treat the parts being manufactured) is conveniently placed near the probe 12 and a tank a quenching medium 32 being evaluated.

In operation, the probe 12 is heated to an appropriate temperature, such as, for example, 1500° F. by the heat source 28. The microcomputer 20 may be programmed to sound the alarm 24 when the desired temperature, which may be input by the data input terminal 22, is reached in order to indicate to the operator that the system is ready to test the quenching medium 32. Once the probe 12 has been heated to the desired temperature, the probe 12 is immersed in the quenching medium 32 and a cooling curve showing temperature versus time, as shown in FIG. 2, or a cooling rate curve showing cooling rate as a function of temperature, as shown in FIG. 3, or both are plotted. The data is then automatically (and visually if desired) analyzed to determine whether the cooling rate is within predetermined boundaries at various temperatures. The need for determining whether the cooling rate is between predetermined boundaries mainly arises because most ferrous metals such as iron and steel change phases as they cool, and the cooling rate must be carefully selected, particularly at critical areas at which the phase is apt to change so that the desired phase is obtained. Typical critical zones are illustrated by the windows 34, 36 and 38 in FIG. 2. The window 36 is critical since the cooling rate in the window 34 provides an indication of the initial slope of the cooling curve, and provides an indication as to whether the rate of subsequent cooling will be such as to put the cooling curve through desired regions in the temperature transformation diagram. Windows such as 36 and 38 may be placed around particularly critical areas of the temperature transformation diagram in order to check whether or not the cooling curve does actually pass through the desired areas. Corresponding windows on the rate curve (FIG. 3) are designated as 34', 36' and 38'.

Of the two diagrams illustrated in FIGS. 2 and 3, the temperature versus time curve is useful in design work for determining the cooling rate necessary for the cooling curve to pass through or to miss various regions on the temperature transformation diagram. Thus, the temperature versus time diagram can be interposed over a temperature transformation diagram to determine which phases (e.g., austenite, bainite or pearlite) will be formed for cooling various curves. Conversely, the cooling characteristics can be tailored as necessary to provide a desired metal composition.

Once the desired slope of the temperature versus time curve has been determined, the temperature versus time curve may be differentiated to generate a temperature versus cooling rate curve of the type illustrated in FIG. 3. Once this has been done, the allowable windows, such as windows 34', 36' and 38' may be determined and the allowable range of rates over the various temperature regions may be entered into the microcomputer 20 (FIG. 1) via the data input terminal 22.

The device 10 according to the invention may be operated both in a design mode and in a quenching medium checking mode. In the design mode, the probe 12 may be fabricated in the shape of the actual production part that is to be quenched, and made from the same material as the production part. The probe may then be heated and quenched and the composition of the quenchant 32 adjusted until the desired quenching characteristics are obtained. Alternatively, the probe may be made in the same shape as the production part, but fabricated from a material such as stainless steel or nickel that does not change phase during the quenching operation. When a different material is used for the probe, the desired quench rate must be renormalized for the difference in thermal conductivities of the materials. This is a linear transformation and can be done simply within the microcomputer 20 if the thermal conductivities of the probe material and the production part are known. In addition, the probe 12 need not be made the same geometric shape as the production part, but may be a simple shape such as a cylinder or the like. In this event, the effect on the cooling curve caused by the difference in geometry between the probe and production part will have to be calculated; however, to normalize for the geometric characteristics is more difficult than is the renormalization for thermal conductivity, and may even have to be done empirically.

In the quenching medium testing mode of operation, where the quenching medium 32 is periodically checked during production, the geometric effects of the probe 12 are not important, and a very simply probe, such as a cylindrical probe, may be used as the probe 12. The reason for this is that when good parts, as determined by other methods, are being produced, the quenching medium is assumed to be good. Consequently, a cooling curve measured by the probe 12 when good parts are being produced is presumed to be representative of a good quenching medium, regardless of its actual shape. However, any deviation of the cooling curve from the cooling curve produced when good parts are being measured represents a deviation in the quality of the quenching medium. Therefore, in the quenching medium checking mode of operation, the cooling curve is measured, and the cooling rates at critical areas determined. Windows are then defined about these critical areas and entered into the microcomputer. It does not matter whether or not the cooling curve measured by the probe 12 is the same as the cooling curve of the production part. All that matters is that the cooling curve measured by the probe 12 does not deviate substantially during subsequent tests, since such deviation indicates a change in the quenching medium which could be of sufficient magnitude to cause the parts being manufactured to be improperly quenched. Thus, in the quenching medium testing mode, no renormalization is required, and the quality of the quenching medium is readily measured by measuring the cooling curve of a simple probe when good parts are being made, defining windows about critical areas of the cooling curve and sounding an alarm if the cooling curve passes outside of any of the windows (e.g. windows 38 and 38'; FIGS. 2 and 3). Also, the cooling curve and the cooling rate curve of the various tests may be plotted via the plotter/printer 26 to determine whether the curves are approaching the boundaries of any of the windows so that future problems may be anticipated before they actually occur.

Obviously, many modifications and variations of the of the present invention are possible in light of the above teachings. Thus, it is to be understood that, within the scope of the appended claims, the invention may be practiced otherwise than as specifically described above.

What is claimed and desired to be secured by Letters Patent of the United States is:

1. A method for determining an appropriate quenching medium for producing predetermined characteristics in a production part comprising the steps of:

determining the desired characteristics of the production part;

defining on a temperature transformation diagram the cooling characteristic required to obtain said desired characteristic;

immersing a heat test probe into a quenching medium and measuring the time versus temperature characteristic of the test probe, where said test probe has the same shape and same thermal conductivity as said production part; and adjusting the characteristic of the quenching medium until the desired time versus temperature characteristic is obtained.

* * * * *